United States Patent
Kamohara

(10) Patent No.: US 7,380,977 B2
(45) Date of Patent: Jun. 3, 2008

(54) DENTAL IMPRESSION MATERIAL KNEADING DEVICE

(75) Inventor: Hiroshi Kamohara, Tokyo (JP)

(73) Assignee: GC Corporation, Tokyo (JP)

( * ) Notice: Subject to any disclaimer, the term of this patent is extended or adjusted under 35 U.S.C. 154(b) by 371 days.

(21) Appl. No.: 11/075,865

(22) Filed: Mar. 10, 2005

(65) Prior Publication Data

US 2006/0120210 A1 Jun. 8, 2006

(30) Foreign Application Priority Data

Mar. 12, 2004 (JP) .............................. 2004-071100

(51) Int. Cl.
*B01F 15/02* (2006.01)
(52) U.S. Cl. ................. 366/160.3; 366/181.8
(58) Field of Classification Search ............... 366/76.6, 366/76.93, 160.2, 160.3, 160.4, 181.8, 182.2
See application file for complete search history.

(56) References Cited

U.S. PATENT DOCUMENTS

| | | | | |
|---|---|---|---|---|
| 3,076,637 | A * | 2/1963 | Moziek et al. ........... | 366/160.3 |
| 5,482,368 | A * | 1/1996 | Nakamura et al. ........ | 366/152.2 |
| 6,394,643 | B1 * | 5/2002 | Bublewitz et al. ........ | 366/172.1 |
| 2003/0123323 | A1 | 7/2003 | Bublewitz et al. | |
| 2003/0137898 | A1 * | 7/2003 | Wagner et al. ........... | 366/172.1 |
| 2005/0226095 | A1 * | 10/2005 | Wagner et al. .............. | 366/194 |

FOREIGN PATENT DOCUMENTS

| | | |
|---|---|---|
| DE | 26 44 931 | 4/1978 |
| JP | 2000-116675 | 4/2000 |
| JP | 2000-117080 | 4/2000 |
| JP | 2000-140600 | 5/2000 |

* cited by examiner

*Primary Examiner*—David Sorkin
(74) *Attorney, Agent, or Firm*—Oblon, Spivak, McClelland, Maier & Neustadt, P.C.

(57) ABSTRACT

To provide a dental impression material kneading device for discharging each paste of a dental impression material comprising two kinds of pastes having different fluidities at the time of feed start with a mixing ratio selected and set among two or more gradual mixing ratios, and mixing and kneading each paste in a mixer body, the device comprises a prescribed rate feed pump 4 for feeding one paste at a fixed flow rate, a set rate feed pump 5 for feeding another paste at a flow rate more than that of the prescribed rate feed pump 4, and a control means 8 for rotatively driving a rotational axis for engaging a stirring rod 2a when receiving a signal from a starting switch 8a, collating starting times of both pumps 4 and 5 corresponding to mixing ratio selected and set by a mixing ratio selection switch 6 corresponding to two or more gradual mixing ratios memorized in the starting time memory means 7, starting the both pump 4 and 5, and feeding the paste at the flow rate corresponding to the selected and set mixing ratio by the set rate feed pump 5.

7 Claims, 3 Drawing Sheets

DENTAL IMPRESSION MATERIAL KNEADING DEVICE

BACKGROUND OF THE INVENTION

1. Field of the Invention

The present invention relates to a dental impression material kneading device for discharging two kinds of pastes of a dental impression material respectively, and mixing and kneading the both pastes in a mixer body. The dental impression material comprises the two kinds of pastes having different fluidities at the time of a feed start, and the mixer body comprises a stirring rod and an outer case mounted around the stirring rod.

2. Description of the Conventional Art

As a general dental impression material comprising the two kinds of pastes, a dental alginate impression material, a dental silicone rubber impression material and the like are commonly known. The dental alginate impression material is made by kneading a substrate paste containing alginic acid salt as a main component and a curing agent paste containing gypsum as a main component. The dental silicone rubber impression material is made by mixing and kneading a substrate paste and a curing agent paste. The substrate paste contains silicone having Si—H group and silicone having a vinyl group as main components. The curing agent paste contains silicone having a vinyl group and a platinum catalyst as main components.

Further, such the conventional dental impression material comprising two kinds of pastes is made by mixing and kneading each paste with a fixed mixing ratio beforehand. However, in recent years, the dental impression material comprising the two kinds of pastes, where a viscosity of the dental impression material in a paste state after mixing and kneading can be arbitrarily adjusted by mixing and kneading the two kinds of pastes at a changed mixing ratio of each paste within the prescribed range was developed. (Hereinafter, "this dental impression material comprising the two kinds of pastes, where a viscosity of the pastes of the dental impression material can be arbitrarily adjusted after mixing and kneading by changing the mixing ratio of each paste within the prescribed range" is said to as "the dental impression material having the arbitrarily adjusted viscosity".) In the case of mixing and kneading such the dental impression material having the arbitrarily adjusted viscosity, the material may be mixed and kneaded after each paste being discharged so as to have the mixing ratio of the both pastes of, for example, 1:3, 1:6, 1:9 or the like, in order to obtain a dental impression material having the desired viscosity after mixing and kneading.

As a device for mixing and kneading such the dental impression material comprising two kinds of pastes, there has been widely used a dental impression material kneading device comprising two parts, one of which discharges each paste of the dental impression material comprising the two kinds of pastes, and the other of which mixes and kneads the both pastes in a mixer body comprising a stirring rod and an outer case mounted around the stirring rod. More particularly, for example, the device comprising a paste feed means, an outer case, a stirring rod and a rotation means (for example, referring to Japanese Patent Laid Open No. 2000-116675) is used. The paste feed means comprises a first paste flow passage extending to a first paste outlet opened at a front end face, and a second paste flow passage extending to a second paste outlet opened at the front end face. The outer case comprises a cylindrical main part arranged at the downstream side of the front end face of the paste feed means. The stirring rod is rotatably provided in the outer case, having a central axis at a center of the outer case. The rotation means is for stirring by the stirring rod. In this device, when the first paste flowing from the first paste outlet and the second paste flowing from the second paste flow passage pass between the outer case and the stirring rod to flow, these pastes are kneaded by the rotated stirring rod.

However, when such the dental impression material kneading device is used to mix and knead the both pastes of the dental impression material comprising the two kinds of pastes, there are following problems. That is, the two kinds of pastes of the dental impression material have generally different fluidities at the time of feed start since they have different characteristics about moving from a static state respectively. Thus, when each paste is discharged into the outer case of the mixer body in the initial stage of the mixing and kneading, the paste having the low fluidity at the time of feed start is discharged later than the paste having the high fluidity at the time of feed start, so that a time difference is generated. Thus, the dental impression material discharged from an outlet of the outer case of the mixer body in the initial stage is a defective material which is not suitable to make the impression or the like, since the mixing ratio of the both pastes greatly differs from the ratio prescribed beforehand by the time difference at the time of feed start, and thus this material cannot be used and becomes a waste.

Further, when the dental impression material comprising the two kinds of pastes to be mixed and kneaded is the dental impression material having the arbitrarily adjusted viscosity, there are following problems. That is, the time difference generated when the paste having the low fluidity at the time of feed start and the paste having the high fluidity at the time of feed start are discharged into the outer case of the mixer body changes by changing of the mixing ratio of the both pastes even in the case of the same dental impression material. Thus, when the dental impression material having the arbitrarily adjusted viscosity is mixed and kneaded by using such the dental impression material kneading device, the dental impression material discharged from the outlet of the outer case of the mixer body is a defective material which is not suitable to make the impression material or the like, whatever mixing ratio of the discharged pastes may be, since the mixing ratio of the both pastes greatly differs from the desired ratio in the initial stage of the mixing and kneading, and thus such the dental impression material can not be made readily to use.

Then, for solving the time difference generated when the pastes respectively having the low and high fluidities at the time of feed start are discharged into the outer case of the mixer body, and for obtaining the dental impression material comprising the two kinds of pastes in the desired preferable mixing and kneading state in the initial stage of the mixing and kneading, the following mixer body, in which the outer case thereof to be mounted in a dental impression material kneading device is improved, (for example, refer to Japanese Patent Laid Open No. 2000-117080) was proposed, that is, the mixer body comprising a container having a horizontal axis, openings for taking-in each component at a rear end and an injection opening at a front thereof, and a mixing chamber formed in the container, wherein a delay chamber is provided between one of the taking-in openings in the container and the mixing chamber, and extends around the horizontal axis in an arc-shape so as to elongate a passage for flowing one component taken in from one of the taking-in openings.

In this mixer body, the time difference generated when the pastes respectively having the low and high fluidities at the time of feed start are discharged into the outer case of the mixer body can be solved, whereby the dental impression material comprising the two kinds of pastes in the desired preferable mixing and kneading state can be obtained in the initial stage of the mixing and kneading. However, there are following problems. That is, since the delay chamber, which extends around the horizontal axis in the arc-shape so as to elongate the passage for flowing one component taken in from one of the taking-in openings, exists, the paste remained in the mixer body cannot be removed after using, and thus this mixer body cannot be reused. Thus, an unused mixer body must be prepared whenever mixing and kneading, and it is uneconomical. Further, since the used mixer body is thrown away, there is much futility and the time for disposing the waste increases. Furthermore, even if the mixer body has the structure where the delay chamber can be detached, there are following problems. That is, since the delay chamber itself has the complicated structure, a cleaning work for removing the pastes remained in the mixer body, the delay chamber or the like after using, takes time and labor, and thus the time and a labor are spent uselessly. Further, if a time and a labor for carrying out the cleaning work are considered, it may be more economical that the used mixer body is disposed without the cleaning work for removing the remained pastes.

Furthermore, in the case of changing the mixing ratio of each paste of the dental impression material having the arbitrarily adjusted viscosity, there are following problems. That is, the time difference, which is generated when the pastes respectively having the low and high fluidities at the time of feed start are discharged, changes with the mixing ratio of the both pastes. Thus, in order to obtain the dental impression material comprising the two kinds of pastes where the material has the desired mixing ratio and is in the preferable mixing and kneading state in the initial stage of the mixing and kneading, two or more outer cases corresponding to each mixing ratio of the both pastes must be prepared, where each of these outer cases have the delay chamber having the length corresponding to the time difference generated when the pastes respectively having the low and high fluidities at the time of feed start are discharged, so that it is uneconomical. Further, since the outer case corresponding to the mixing ratio of the pastes must be selected and replaced whenever the mixing ratio of the both pastes is changed, it takes time and labor so much, and thus it is not practical.

On the other hand, for solving the time difference generated when the pastes respectively having the low and high fluidities at the time of feed start are discharged into the outer case of the mixer body, and for obtaining the dental impression material comprising the two kinds of pastes in the desired preferable mixing and kneading state in the initial stage of the mixing and kneading, the following dental impression material kneading device with improvement in itself (for example, refer to Japanese Patent Laid Open No. 2000-140600) was proposed. That is, the device comprising, for example, a first paste supply source, a second paste supply source, a kneading means, a first feed pump for feeding a first paste in the first paste supply source to the kneading means through a first paste flow passage, a second feed pump for feeding a second paste in the second paste supply source to the kneading means through a second paste flow passage, a first electric motor for driving the first feed pump, a second electric motor for driving the second feed pump, and a control means for controlling an operation of the first electric motor and the second electric motor, wherein the control means makes the required time difference between rotation starts of the first electric motor and the second electric motor, thereby, although the first and second pastes have the different viscosities and feed flow rates each other, these pastes reaches the kneading means almost simultaneously at the time of feed start, at least one of the first electric motor and the second electric motor is a variable speed electric motor, and the control means adjusts the ratio of a rotational rate of the first electric motor and a rotational rate of the second electric motor, to set the ratio of the feed flow rates of the first paste and the second paste as the prescribed value.

This device solves the time difference generated when the pastes respectively having the low and high fluidities at the time of feed start are discharged into the outer case of the mixer body, and the dental impression material comprising the two kinds of pastes in the desired preferable mixing and kneading state can be obtained in the initial stage of the mixing and kneading. However, when the mixing ratio of the each paste of the dental impression material having the adjusted arbitrarily viscosity is changed in such the device, there are following problems. That is, the time difference, which is generated when the pastes respectively having the low and high fluidities at the time of feed start are discharged, changes with the mixing ratio of the both pastes. Thus, whenever the mixing ratio of the both pastes is changed, setting of the required time difference between the rotation starts of the first electric motor and the second electric motor carried out by the control means, and setting of the ratio of the rotational rates of the first electric motor and the second electric motor must be changed, and thus it takes time and labor so much. Further, when an operator does not understand the time difference or sets this time difference erroneously, it is impossible to obtain the dental impression material having the desired mixing ratio in the preferable mixing and kneading state in the initial stage of the mixing and kneading.

SUMMARY OF THE INVENTION

The present invention solves the above-mentioned problems of the conventional techniques, and the primary objective is to provide an easy and convenient dental impression material kneading device for discharging respectively two kinds of pastes of a dental impression material comprising the two kinds of pastes having different fluidities at the time of a feed start, and mixing and kneading the both pastes in a mixer body comprising a stirring rod and an outer case mounted around the stirring rod. More particularly, the device is to make it possible to obtain a dental impression material having a desired mixing ratio of the two kinds of pastes in the preferable mixing and kneading state in the initial state of the mixing and kneading, even when the material is the dental impression material having the adjusted arbitrarily viscosity.

The earnest work was carried out in order to solve the above mentioned problems and, as the result, the present inventors found out that the dental impression material having the desired mixing ratio in the preferable mixing and kneading state can be obtained in the initial stage of the mixing and kneading, even when this dental impression material having the adjusted arbitrarily viscosity, by the process comprising: feeding one paste of the dental impression material by a prescribed rate feed pump at a fixed flow rate, where the material comprises the two kinds of pastes having different fluidities at the time of feed start; feeding the another paste by a set rate feed pump at a flow rate gradually selected to be more than that of the prescribed rate feed pump; pre-memorizing starting times of the prescribed rate feed pump and the set rate feed pump in a starting time memory means, where these times correspond to two or more gradual mixing ratios of the both pastes; collating the starting times memorized in the starting time memory means, where these times correspond to a mixing ratio selected and set by a mixing ratio selection switch; starting the prescribed rate feed pump and the set rate feed pump according to the collated starting times; and controlling the set rate feed pump so as to feed the paste at the flow rate corresponding to the mixing ratio selected and set by the mixing ratio selection switch. The mixing selection switch is for selecting and setting the mixing ratio of the both pastes to arbitrary one mixing ratio among the two or more gradual mixing ratios. Thereby, each paste can be discharged into the mixer body with the time difference corresponding to the selected and set mixing ratio at the time of feed start, and fed at the flow rate corresponding to the selected and set mixing ratio, by only an easy operation where the mixing ratio of the both pastes is selected and set to arbitrary one mixing ratio in the two or more gradual mixing ratios by the mixing ratio selection switch. Then, the present invention was completed.

That is, the present invention relates to a dental impression material kneading device for discharging each paste of the dental impression material comprising the two kinds of pastes having different fluidities at the time of feed start with the mixing ratio selected and set among the two or more gradual mixing ratios, and for mixing and kneading the both pastes in the mixer body. The mixer body comprises the stirring rod for mixing and kneading, and the outer case mounted around the stirring rod. This dental impression material kneading device comprises a pair of inlets, a pair of outlets, a prescribed rate feed pump, a set rate feed pump, a mixing ratio selection switch, a starting time memory means, and a control means. Into the pair of inlets, each paste is supplied from a container accommodating each paste. The pair of outlets is provided at a mixer body mounting part comprising a rotational axis for engaging a stirring rod and an outer case mounting part, the rotational axis being projected for detachably engaging the stirring rod, and the outer case mounting part being for detachably mounting the outer case. The prescribed rate feed pump is for feeding one of the pastes at a fixed flow rate from one of the inlets to one of the outlets. The set rate feed pump is for feeding the other of the pastes at a flow rate gradually selected to be more than that of the prescribed rate feed pump, from the other of the inlets to the other of the outlets. The mixing ratio selection switch is for selecting and setting the mixing ratio of the both pastes to be arbitrary one mixing ratio among the two or more gradual mixing ratios. In the starting time memory means, starting times of the prescribed rate feed pump and the set rate feed pump are prememorized, and these times correspond to the two or more gradual mixing ratios of the both pastes. The control means is for rotatively driving the rotational axis for engaging the stirring rod when receiving a signal for starting the mixing and kneading of the both pastes from a starting switch for transmitting the signal, collating the starting times memorized in the starting time memory means corresponding to the mixing ratio selected and set by the mixing ratio selection switch, starting drives of the prescribed rate feed pump and the set rate feed pump according to the collated starting times, and controlling the set rate feed pump so as to feed the paste at a flow rate corresponding to the mixing ratio selected and set by the mixing ratio selection switch.

Further, it is also found that, as for the dental impression material comprising two or more sets of two kinds of pastes having different fluidities at the time of feed start, the viscosity of the dental impression material can be arbitrary adjusted by changing a mixing ratio of the two or more sets of the both pastes within the prescribed range through an easy operation of selecting and setting, by a dental impression material selection switch, arbitral one of dental impression materials comprising two kinds of pastes having different fluidities at the time of feed start among dental impression materials comprising two or more sets of two kinds of pastes having different fluidities at the time of feed start. For this purpose, the starting times of the prescribed rate feed pump and the set rate feed pump corresponding to the two or more gradual mixing ratios of the both pastes, are pre-memorized in the starting time memory means, and the control means collates the starting times memorized in the starting time memory means, starts the prescribed rate feed pump and the set rate feed pump according to the collated starting times, and controls the set rate feed pump to feed the paste at a flow rate corresponding to the mixing ratio selected and set by the mixing ratio selection switch with respect to a dental impression material selected and set by the dental impression material selection switch for selecting and setting arbitrary one among two or more sets of dental impression materials.

The dental impression material kneading device according to the present invention comprises the above-mentioned constitutions. Thus, the dental impression material comprising the two kinds of pastes, which has the desired mixing ratio in the preferable mixing and kneading state, can be made in the initial stage of the mixing and kneading, only by the easy operation of the mixing ratio selection switch that the mixing ratio of the both pastes is selected and set to the arbitrary one mixing ratio among the two or more gradual mixing ratios, even when this material is the dental impression material having viscosity which is arbitrarily adjustable by changing a mixing ratio of both pastes within the prescribed range. Further, the dental impression material kneading device according to the present invention can make the dental impression material comprising the two kinds of pastes having the desired mixing ratio in the preferable mixing and kneading state by using an easily reusable general mixer body without using a mixer body having a complicated structure which is difficult to clean for removing the remained pastes, expensive, and hardly reused. Then, the running cost can be made low, so that it is excellent in economic view point. The time and labor for disposing the used mixer bodies can be decreased. Further, even if an operator does not know of the time difference generated by the difference of the fluidities of the two kinds of pastes, the operator need not set the time difference, the feed rate of the prescribed rate feed pump and the set rate feed pump, or the like respectively, since the starting times of the prescribed feed pump and the set rate feed pump corresponding to the two or more gradual mixing ratios of the both pastes are prememorized in the starting time memory means. The operator only selects and sets the arbitrary one mixing ratio by the mixing ratio selection switch among the two or more gradual mixing ratios. Then, the operatability is remarkably increased, and it can be completely prevented that the dental impression material is wasted by mistaking the setting of the mixing ratio, the time difference or the like.

Furthermore, as mentioned above, the dental impression material kneading device according to the present invention is suitable for mixing and kneading the dental impression material having the arbitrarily adjusted viscosity in the preferable state where the mixing ratio of the two kinds of pastes is the desirable ratio in the initial stage of the mixing and kneading. Further, even in the case of the conventional dental impression material comprising the two kinds of pastes in which each paste is mixed and kneaded with the fixed mixing ratio, when the mixing ratio of the both pastes is selected and set to the fixed mixing ratio among the two or more gradual mixing ratios by the mixing ratio selection switch, each paste can be discharged into the mixer body with the time difference corresponding to the selected and set mixing ratio at the time of feed start, and each paste can be fed at the flow rate corresponding to the selected and set mixing ratio. Thus, it is possible to make the dental impression material having the fixed mixing ratio of the two kinds of pastes in the preferable mixing and kneading state in the initial stage of the mixing and kneading.

Furthermore, as for the dental impression material comprising two or more sets of two kinds of pastes having different fluidities at the time the feed start, the viscosity of the dental impression material can be arbitrary adjusted by changing a mixing ratio of the two or more sets of the both pastes within the prescribed range through an easy operation of selecting and setting, by a dental impression material selection switch, arbitral one of dental impression materials comprising two kinds of pastes having different fluidities at the time of feed start among dental impression materials comprising two or more sets of two kinds of pastes having different fluidities at the time of feed start. For this purpose, the starting times of the prescribed rate feed pump and the set rate feed pump corresponding to the two or more gradual mixing ratios of the both pastes, is pre-memorized in the starting time memory means, and, the control means collates the starting times memorized in the starting time memory means with respect to a dental impression material selected and set by the dental impression material selection switch for selecting and setting arbitrary one among two or more sets of dental impression materials, starts the prescribed rate feed pump and the set rate feed pump according to the collated starting times, and controls the set rate feed pump to feed the paste at a flow rate corresponding to the mixing ratio selected and set by the mixing ratio selection switch. The device according to the present invention can correspond to such the dental impression material comprising the two kinds of pastes having viscosity which is arbitrarily adjustable by changing a mixing ratio of both pastes within the prescribed range, so that it is not necessary for each set of the dental impression material to prepare the different device respectively.

EXPLANATION OF CODES $1x$ and $1y$ are inlets, 2 is a mixer body mounting part, $2a$ is a rotational axis for engaging a stirring rod, $2b$ is an outer case mounting part, $3x$ and $3y$ are outlets, 4 is a prescribed rate feed pump, 5 is a set rate feed pump, 6 is a mixing ratio selection switch, 7 is a starting time memory means, 8 is a control means, $8a$ is a starting switch, 9 is a dental impression material selection switch, Cx and Cy are containers, M is a mixer body, K is a stirring rod, K1 is a stirring blade, S is an outer case, and S1 is a discharging gate.

DETAILED DESCRIPTION OF PREFERRED EMBODIMENT

Hereinafter, the dental impression material kneading device according to the present invention is explained concretely with reference to examples and drawings.

Figure 1:
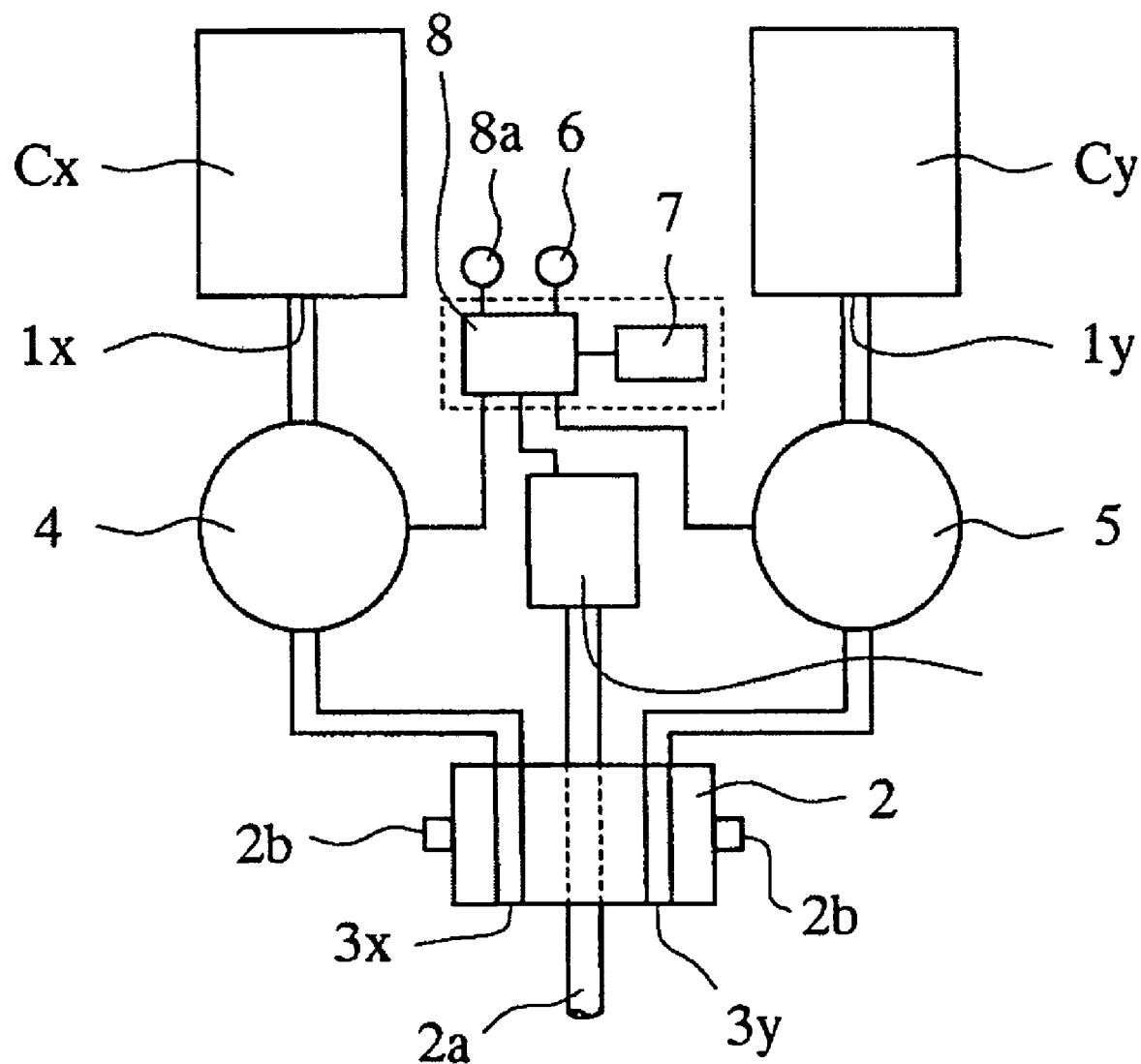
FIG. 1 is an explanatory view schematically showing one example of a structure of the dental impression material kneading device according to the present invention.
Figure 2:
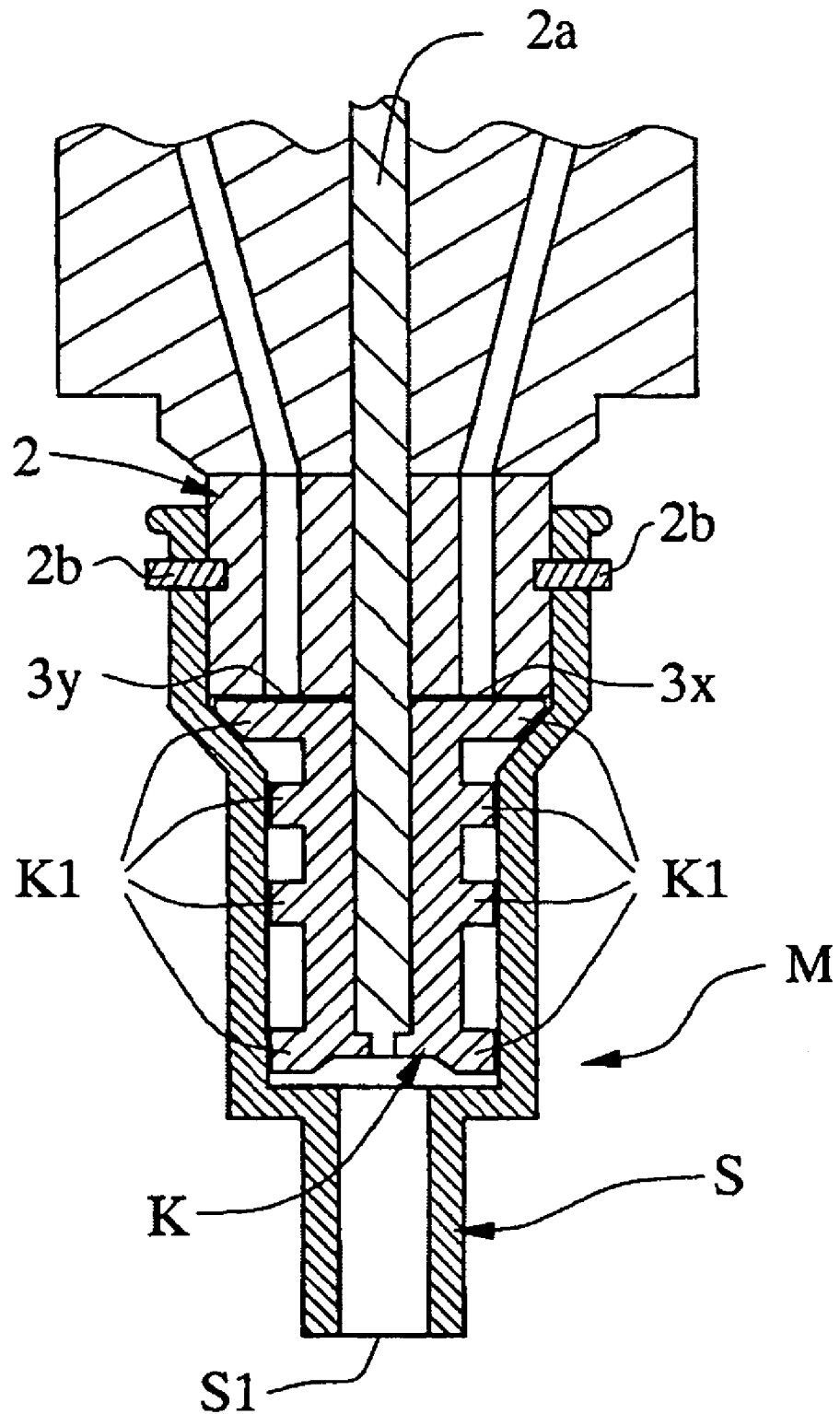
FIG. 2 is an explanatory view of a front cross-sectional part showing one example, in which the mixer body is mounted at the mixer body mounting part of the dental impression material kneading device according to the present invention.
Figure 3:
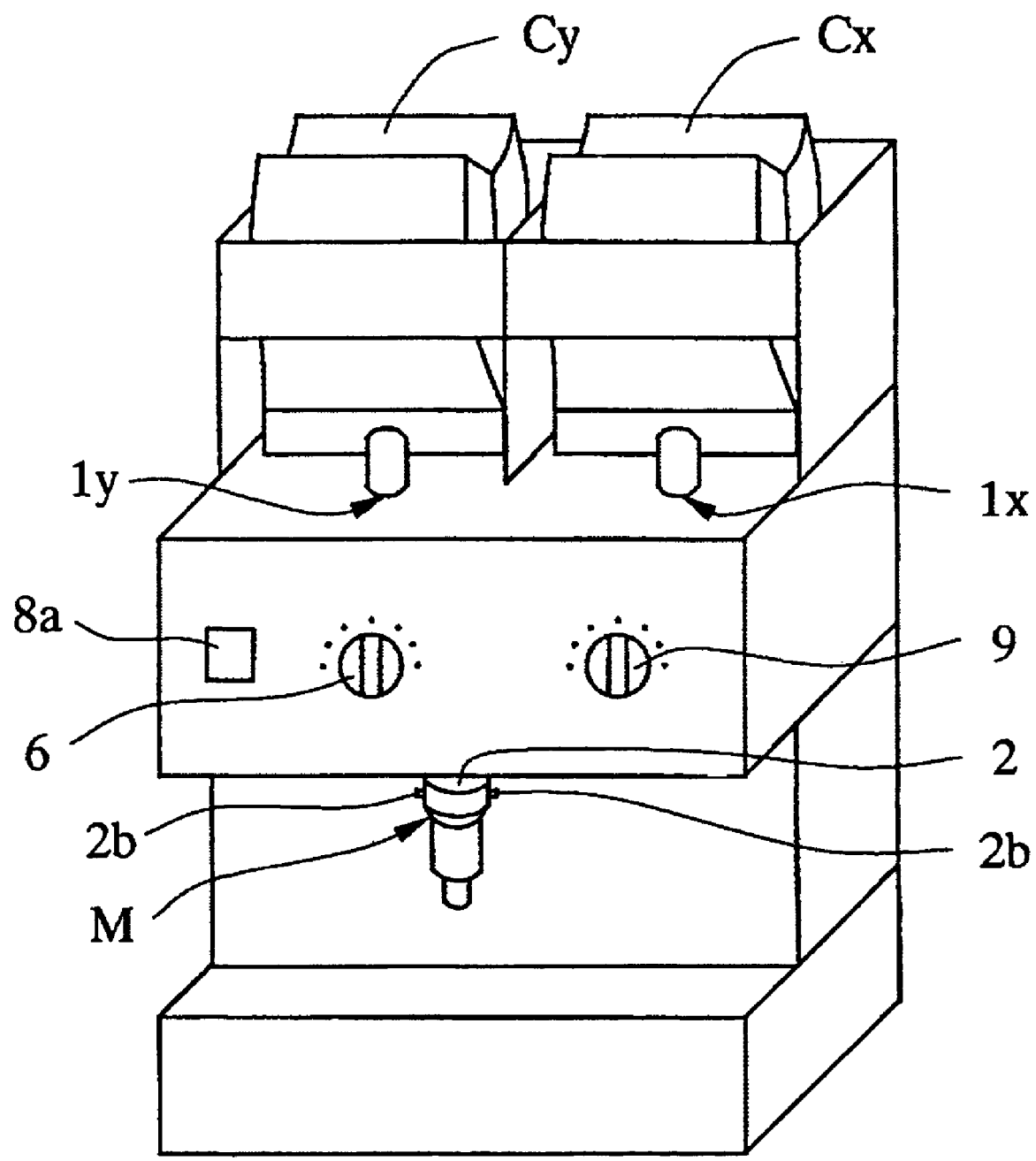
FIG. 3 is a perspective view in which the containers accommodating each paste for dental impression material comprising the two kinds of pastes and the mixer body are mounted in the dental impression material kneading device according to the present invention.

FIG. 1 is an explanatory view schematically showing one example of a structure of the dental impression material kneading device according to the present invention. FIG. 2 is an explanatory view of a front cross-sectional part showing one example, in which the mixer body is mounted at the mixer body mounting part of the dental impression material kneading device according to the present invention. FIG. 3 is a perspective view, where the containers and the mixer body are mounted in the dental impression material kneading device according to the present invention, and the container accommodates each paste for dental impression material comprising the two kinds of pastes.

In the drawings, $1x$ and $1y$ are one pair of inlets, through which each paste of the dental impression material comprising the two kinds of pastes having different fluidities at the time of feed start is fed from containers Cx and Cy accommodating each paste. The inlets $1x$ and $1y$ are for flowing each fed paste into one pair of outlets $3x$ and $3y$ mentioned below.

As the inlets $1x$ and $1y$, any form may be used if this form is made so as to receive the supplying of each paste of the dental impression material comprising the two kinds of pastes having the different fluidities at the time of feed start, from the containers Cx and Cy. However, in order to prevent mixing of air into each supplied paste when receiving the supplying of each paste from the containers Cx and Cy, it is preferable that the inlets $1x$ and $1y$ have a form where the discharging gates of the containers Cx and Cy for each paste can be engaged. For example, when the discharging gates of the containers Cx and Cy have an only cylindrical form, it is preferable that the inlets $1x$ and $1y$ have a cylindrical form so as to fit with the discharging gates of the containers Cx and Cy. When the discharging gates of the containers Cx and Cy have the cylindrical forms and have a male screw at outer peripheral face thereof, it is preferable that the inlets $1x$ and $1y$ have a form having a female screw at inner face thereof so as to screw the discharging gates of the containers Cx and Cy into the inlets.

Further, as the containers Cx and Cy for supplying the pastes to the inlets $1x$ and $1y$, a container such as a bag comprising a flexible synthetic resin or the like, in which the discharging gate is attached, is preferably used in order to prevent to enter air into the containers Cx and Cy as much as the volume of the pastes flowed into the mixer body when supplying the pastes to the inlets $1x$ and $1y$, as shown in FIG. 2. Further, as shown in FIG. 3, it is desirable that a supporting member is provided so as to direct the discharging gates of the containers Cx and Cy downward to engage with the inlets $1x$ and $1y$.

As shown in FIGS. 1 and 2, 2 is a mixer body mounting part comprising a rotational axis for engaging a stirring rod $2a$ and an outer case mounting part $2b$. The rotational axis for engaging a stirring rod $2a$ is projected in order to detachably mount a stirring rod K. The outer case mounting part 2b is for detachably mounting an outer case S. The mixer body mounting part 2 has the one pair of the outlets 3y and 3x mentioned below, and is for mixing and kneading each paste discharged from the one pair of the outlets 3y and 3x in a mixer body M, which is detachably mounted.

Each paste discharged from the one pair of the outlets 3y and 3x mentioned below flows into the outer case S of the mixer body M, which is mounted at the outer case mounting part 2b of the mixer body mounting part 2. The both pastes flowed into the outer case S of the mixer body M is mixed and kneaded by rotatively driving the stirring rod K of the mixer body M, which is mounted at the rotational axis for engaging the stirring rod 2a of the mixer body mounting part 2. Then, the pastes are discharged from the outer case S of the mixer body M.

If the outer case mounting part 2b of the mixer body mounting part 2 has a form such as, for example, an engagement piece projected from an outer peripheral face of the mixer body mounting part 2 as shown in FIGS. 1 and 2, so as to engage with a groove engaging part provided at a base end part of the outer case S of the mixer body M mounted, the outer case S can be certainly mounted to the mixer body mounting part 2, and thus it is preferable.

The mixer body M mounted to the mixer body mounting part 2 comprises the stirring rod K and the outer case S. The stirring rod K is for mixing and kneading the both pastes, and the outer case S is mounted around the stirring rod K. For example, as shown in FIG. 2, if the mixer body M is a general one capable to be easily reused, it is preferable to use. In this general mixer body M, the outer case S comprises a base end part in a large inner diameter cylindrical shape, a kneading part in a middle inner diameter cylindrical shape and a discharging gate S1 in a small inner diameter cylindrical shape. The kneading part is connected with the base end part through a throttled part in a tapered conical cylindrical shape. The stirring rod K is mounted to the rotational axis for engaging the stirring rod 2a, which is projected from the mixer body mounting part 2. On a cylindrical outer face of the rotational axis for engaging the stirring rod 2a, two or more sets of a stirring blade K are projectingly provided. The mixer body M can be reused repeatedly, and thus the running cost can be made low, and it is excellent in economical view point. The time and labor for disposing the used mixer body can be decreased, so that it is preferable.

3x and 3y are one pair of the outlets provided at the mixer body mounting part 2. The one pair of the outlets 3x and 3y is for discharging each paste into the outer case S of the mixer body M. The each paste is supplied from the containers Cx and Cy through the one pair of the inlets 1x and 1y to one pair of the outlets 3x and 3y. The container accommodates each paste of the dental impression material comprising the two kinds of pastes having the different fluidities at the time of feed start. The mixer body M is mounted to the mixer body mounting part 2.

Further, as shown in FIG. 1, the outlet 3x being one of the pair of the outlets 3x and 3y is for discharging one paste fed from the inlet 1x by a prescribed rate feed pump 4 mentioned below, where one paste is supplied from the container Cx through the inlet 1x. The outlet 3y being another one is for discharging another paste fed from the inlet 1y by a set rate feed pump 5 mentioned below, where another paste is supplied from the container Cy through the inlet 1y.

As shown in FIG. 2, the pair of outlets 3x and 3y may be provided at point symmetry positions each other with respect to the axial center of the rotational axis for engaging the stirring rod 2a of the mixer body mounting part 2. Further, although not shown in drawings, these outlets 3x and 3y may be provided at not point symmetry positions each other.

4 is a prescribed rate feed pump for feeding one paste from the inlet 1x to the outlet 3x at a fixed flow rate. The pump 4 is for feeding the one paste accommodated in the container Cx into the outer case S of the mixer body M at the fixed flow rate. The mixer body M is mounted to the mixer mounting part 2.

5 is a set rate feed pump for feeding another paste from the inlet 1y to the outlet 3y at a rate gradually selected more than the flow rate of the prescribed rate feed pump 4. The pump 5 is for feeding the another paste accommodated in the container Cy into the outer case S of the mixer body M at the rate gradually selected. In this way, the both pastes fed into the outer case S of the mixer body M is mixed and kneaded to make the dental impression material by rotatively driving the rotational axis for engaging the stirring rod 2a, where the stirring rod K of the mixer body M is engaged. Then, this dental impression material is discharged from the outer case S by force for feeding another paste into the outer case S of the mixer body M by the set rate feed pump 5, and by force for feeding one paste into the outer case S of the mixer body M by the prescribed rate feed pump 4.

As for the prescribed rate feed pump 4 and the set rate feed pump 5, the starting times are respectively controlled by a control means 8 mentioned below. When these pump start by the control means 8, the prescribed rate feed pump 4 feeds the one paste at only the fixed flow rate. On the other hand, the set rate feed pump 5 is controlled by the control means 8 so as to have the rate gradually selected more than the flow rate of the prescribed rate feed pump 4, and feeds the another paste. Therefore, the both pastes can be discharged into the mixer body M with the mixing ratio selected and set among the two or more gradual mixing ratios, only by controlling the flow rate of the another paste fed by the set rate feed pump 5 so as to have the flow rate gradually selected more than the flow rate of the prescribed rate feed pump 4 by the control means 8, without controlling the flow rate of the prescribed rate feed pump 4.

As for the prescribed rate feed pump 4 and the set rate feed pump 5, these are not limited especially, if these feed pumps are respectively formed at least so as to feed the another paste at the flow rate gradually selected more than the fixed rate of the one paste. However, if the each of the feed pumps 4 and 5 comprises a rotary pump or a trochoid pump and a general driving means, such as a DC motor or an AC motor, it is preferable since these driving means are inexpensive and can easily control the flow rate and the starting. Therefore, the total cost for making the whole device of the present invention can be reduced. The rotary pump or the trochoid pump is suitable for feeding a liquid having a viscosity.

The mixing ratio of the both pastes of the conventional dental impression material comprising the two kinds of pastes having the different fluidities is at the time of feed start generally prescribed within about 1:1-1:7 by volume where it is different by its kind. However, in the present invention, the mixing ratio of the both pastes of the dental impression material having the arbitrarily adjusted viscosity can be adjusted within the range of about 1:1-1:10 by volume in general. So, in the device of the present invention, in order to change easily the mixing ratio of each paste to a desired mixing ratio, the set rate feed pump 5 can feed the another paste at a flow rate, for example, selected from the flow gradual rate such as equal, 3 times, 5 times, 7 times, 9 times, or the like of the flow rate of the one paste fed by the prescribed rate feed pump 4. Then, the mixing ratio selected and set among the two or more gradual mixing ratios, for example, the mixing ratios of 1:1, 1:3, 1:5, 1:7, 1:9 or the like, can be obtained.

6 is a mixing ratio selection switch for selecting and setting the arbitrary one mixing ratio of the both pastes among the two or more gradual mixing ratios. The switch 6 is for collating the starting times of the prescribed rate feed pump 4 and the set rate feed pump 5 memorized corresponding to the selected and set mixing ratio by a starting time memory means 7 mentioned below.

As the mixing ratio selection switch 6, any one may be used, if this switch is for selecting and setting arbitrary one mixing ratio among the two or more gradual mixing ratios, for example, 1:1, 1:3, 1:5, 1:7, 1:9 or the like, and transmitting the selected and set arbitrary one mixing ratio to the control means 8 mentioned below. More particularly, as shown in FIG. 3, when the mixing ratio selection switch 6 is a rotary changeover switch, structure may be made such that the switch comprises an electronic circuit, in which the control means 8 can recognize which mixing ratio of the both pastes is selected and set among the two or more gradual mixing ratios, by assigning each gradual mixing ratio to each contact point of the changeover switch, and electrifying the contact point assigned with the selected and set mixing ratio, when the arbitrary one mixing ratio is selected and set by rotating the changeover switch. Further, as the mixing ratio selection switch 6, for example, structure may also be made such that the switch comprises a mixing ratio selection button, a display means, a mixing ratio setting button and a mixing ratio signal transmission means. In this switch, the mixing ratio selection button is for changing the mixing ratio of the both pastes one by one, the display means is for displaying the changed mixing ratio one by one, the mixing ratio setting button is for selecting and setting the mixing ratio to one displayed in the display means, and the mixing ratio signal transmission means is for transmitting an information signal of the selected and set mixing ratio to the control means 8.

7 is a starting time memory means, in which the starting times of the prescribed rate feed pump 4 and the set rate feed pump 5 are prememorized, and these times correspond to the two or more gradual mixing ratios of the both pastes. In this starting time memory means 7, the starting time corresponding to the mixing ratio selected and set by the mixing ratio selection switch 6 is collated by the control means 8.

In this starting time memory means 7, the starting times of the prescribed rate feed pump 4 and the set rate feed pump 5 are prememorized, where these times correspond to the two or more gradual mixing ratios of the both pastes. When the arbitrary one mixing ratio is selected and set among the two or more gradual mixing ratios of the both pastes by the mixing ratio selection switch 6, the starting time based on this selected and set mixing ratio can be collated by the control means 8, where the starting time is prememorized in the starting time memory means 7.

The starting times of the prescribed rate feed pump 4 and the set rate feed pump 5 are calculated based on the time difference between the necessary times of each paste from starting of each pump until discharging of each paste at respective outlets 3x and 3y, that is, the difference of the time that one paste is discharged from the outlet 3x and the time the another paste is discharged from the outlet 3y when the prescribed rate feed pump 4 and the set rate feed pump 5 start simultaneously for feeding each paste of the dental impression material with the two or more gradual mixing ratios of the both pastes. These starting times are prememorized in the starting time memory means 7 and correspond to the two or more gradual mixing ratios. More particularly, in the case that the dental impression material comprising the two kinds of pastes, where a viscosity can be arbitrarily adjusted by changing the mixing ratio of each paste within the range of, for example, 1:1 to 1:10, is mixed and kneaded with the arbitrary one mixing ratio selected and set by the mixing ratio selection switch 6 among two or more gradual mixing ratios of the both pastes, for example, with the mixing ratio of 1:7, the time from starting the prescribed rate feed pump 4 until discharging the one paste, which is 1 in the mixing ratio 1:7, at the outlet 3x is 1.5 seconds, and the time from starting of the set rate feed pump 5 until discharging of the another paste, which is 7 in the mixing ratio, at the outlet 3y is 0.5 seconds, each paste can be discharged simultaneously from each outlet 3x or 3y, when the set rate feed pump 5 starts 1 second later than the starting of the prescribed feed pump 4. Therefore, the starting times of the prescribed feed pump 4 and the set rate feed pump 5, which correspond to the mixing ratio of 1:7, is that the set rate feed pump 5 starts 1 second later than the starting of the prescribed feed pump 4.

To the contrary, there also is a dental impression material comprising the two kinds of pastes, in which each paste can be simultaneously discharged from each outlet 3x and 3y, when the prescribed rate feed pump 4 starts 1 second later than starting the set rate feed pump 5 for example. In the case of such the dental impression material comprising the two kinds of pastes, the starting times of the prescribed feed pump 4 and the set rate feed pump 5 are that the prescribed rate feed pump 4 starts 1 second later than starting of the set rate feed pump 5. Furthermore, these starting times are changed with the case of changing the mixing ratio of the dental impression material, or depending on the characteristics of the dental impression material itself.

Further, when the starting times of the prescribed rate feed pump 4 and the set rate feed pump 5 corresponding to the two or more gradual mixing ratios of the both pastes are pre-memorized in the starting time memory means 7, the following process may be used. The process comprises, using the time when transmitting the signal for starting the mixing and kneading the both pastes as a starting point, specifying the starting times of the pumps 4 and 5 how many seconds after transmitting the start signal, and prememorizing a data table in the starting time memory means 7. The signal is transmitted by a starting switch 8a in the control means 8 mentioned below. The starting times are specified based on the values calculated for the two or more gradual mixing ratios of the both pastes by the above method. The data table comprises, as shown in Tables 1 to 3, the specified two or more gradual mixing ratios of the both pastes and the specified starting times corresponding thereto of the pump 4 and the pump 5 after the starting switch 8a transmits the start signal.

TABLE 1

| Mixing Ratio of Both Pastes | Starting Time of Prescribed Rate Feed Pump (seconds) | Starting Time of Set Rate Feed Pump (seconds) |
| --- | --- | --- |
| 1:2 | 0.0 | 0.1 |
| 1:3 | 0.0 | 0.2 |
| 1:4 | 0.0 | 0.4 |
| 1:6 | 0.0 | 0.7 |
| 1:7 | 0.0 | 1.0 |

TABLE 2

| Mixing Ratio of Both Pastes | Starting Time of Prescribed Rate Feed Pump (seconds) | Starting Time of Set Rate Feed Pump (seconds) |
| --- | --- | --- |
| 1:2 | 0.5 | 0.7 |
| 1:3 | 0.5 | 0.9 |
| 1:4 | 0.5 | 1.2 |
| 1:6 | 0.5 | 1.7 |
| 1:7 | 0.5 | 2.4 |

TABLE 3

| Mixing Ratio of Both Pastes | Starting Time of Prescribed Rate Feed Pump (seconds) | Starting Time of Set Rate Feed Pump (seconds) |
| --- | --- | --- |
| 1:2 | 0.6 | 0.5 |
| 1:3 | 0.6 | 0.5 |
| 1:4 | 0.7 | 0.5 |
| 1:6 | 0.8 | 0.5 |
| 1:7 | 1.0 | 0.5 |

As shown in Table 1, the starting time of the prescribed rate feed pump 4 may be specified in each mixing ratio so as to start the pump 4 immediately after transmitting the signal for starting the mixing and kneading of the both pastes by the starting switch 8a in the control means 8. Further, for example, as shown in Tables 2 and 3, the starting times of the prescribed feed pump 4 and the set rate feed pump 5 may be specified in each mixing ratio so as to start after passing some times after transmitting the signal by the starting switch 8a and subsequently start the other the prescribed rate feed pump 4 or the set rate feed pump 5 which does not start yet. The starting times of the prescribed rate feed pump 4 and the set rate feed pump 5 corresponding to the two or more gradual mixing ratios, can be suitably specified according to the characteristics of the dental impression material comprising the two kinds of pastes having the different fluidities at the time of feed start and the starting times are prememorized in the starting time memory means 7.

In the later case above, as shown in Tables 2 and 3, for example, that the starting times of the prescribed feed pump 4 and the set rate feed pump 5 are specified so as to start the feed pump 5 or 4 after passing some times in each mixing ratio after transmitting the signal by the starting switch 8a, and then start the other pump which does not start yet, if the rotational axis for engaging the stirring rod 2a starts rotative drive immediately after transmitting the signal for starting the mixing and kneading the both pastes, the both pastes can be discharged into the outer case S of the mixer body M after starting the rotative drive of the stirring rod K of the mixer body M. Therefore, the both pastes can be certainly mixed and kneaded in the initial stage of discharging, and thus it is preferable.

As the starting time memory means 7, it is not especially limited, if it is constituted capable to prememorizing the starting times of the prescribed rate feed pump 4 and the set rate feed pump 5 corresponding to the two or more gradual mixing ratios of the both pastes, and collating, by the control means 8, the starting time corresponding to the mixing ratio selected and set by the mixing ratio selection switch 6. However, for example, if the starting times of the pumps 4 and 5 corresponding to the two or more gradual mixing ratios of the both pastes are memorized in the data table as above mentioned, a memory device such as ROM or the like, it is suitably used.

8 is a control means, which is for rotatively driving the rotational axis for engaging the stirring rod 2a when receiving the signal for starting the mixing and kneading of the both pastes, from the starting switch 8a, collating the starting times corresponding to the mixing ratio selected and set by the mixing ratio selection switch 6, starting of the prescribed rate feed pump 4 and the set rate feed pump 5 according to the collated starting times, and controlling the prescribed rate feed pump 4 so as to feed the paste at the flow rate corresponding to the mixing ratio selected and set by the mixing ratio selection switch 6. The starting switch 8a is for transmitting the signal for starting the mixing and kneading of the both pastes. The starting times are memorized in the starting time memory means 7. Further, the control means 8 is also for controlling the rotative drive of the rotational axis for engaging the stirring rod 2a, the starting times of the prescribed rate feed pump 4 and the set rate feed pump 5, and the flow rate of the prescribed rate feed pump 5, in order to obtain the dental impression material in a preferable state in which the mixing ratio of the dental impression material comprising two kinds of pastes is selected and set by the mixing ratio selection switch 6 to be a desired mixing ratio in the beginning of mixing and kneading.

As shown in FIG. 1, the control means 8 is connected with the starting switch 8a, the mixing ratio selection switch 6, the starting time memory means 7, a drive means, the prescribed rate feed pump 4, and the set rate feed pump 5. The starting switch 8a is for transmitting the signal for starting the mixing and kneading of the both pastes. The mixing ratio selection switch 6 is for selecting and setting the arbitrary one mixing ratio of the both pastes among the two or more gradual mixing ratios. In the starting time memory means 7, the starting times of the prescribed rate feed pump 4 and the set rate feed pump 5 are prememorized, and these times correspond to the two or more gradual mixing ratios of the both pastes. The drive means is for rotatively driving the rotational axis for engaging the stirring rod 2a. The prescribed rate feed pump 4 is for feeding the one paste from the inlet 1x to the out let 3x at the fixed flow rate. The set rate feed pump 5 is for feeding the another paste from the inlet 1y to the outlet 3y at the flow rate gradually selected more than the flow rate of the prescribed rate feed pump 4. The control means 8 is for starting the drive means for rotatively driving the rotational axis for engaging the stirring rod 2a when receiving the signal for starting the mixing and kneading of the both pastes from the starting switch 8a, collating the starting times of the prescribed rate feed pump 4 and the set rate feed pump 5, which correspond to the arbitrary one mixing ratio of the both pastes, in the starting time memory means 7, starting the pumps 4 and 5 according to the collated starting times, and controlling the pump 5 so as to feed the paste at the flow rate corresponding to the mixing ratio. In the above, the arbitrary one mixing ratio is selected and set in the two or more gradual mixing ratios by the mixing ratios selection switch 6.

The control in the control means 8 is explained more particularly. For example, the case that the starting times of the prescribed feed pump 4 and the set rate feed pump 5 are in the data table specified as shown in Table 2, is considered. These times are prememorized in the starting time memory means 7 and correspond to the two or more gradual mixing ratios of the both pastes. When the arbitrary one mixing ratio of the both pastes is 1:3, the control means 8 carries out the following steps. First, when receiving the signal for starting the mixing and kneading the both pastes from the starting switch 8a, the control means starts the drive means for rotatively driving the rotational axis for engaging the stirring rod 2a at first. Next, the control means 8 collates the data of the starting times of the prescribed rate feed pump 4 and the set rate feed pump 5 in the starting time memory means 7 with the transmitted signal, where the data is that the starting times of the pumps 4 and 5 corresponding to the mixing ratio of 1:3 are 0.5 seconds and 0.9 seconds respectively. The transmitted signal is that the mixing ratio selected and set by the mixing ratio selection switch 6 is 1:3. Then, the control means 8 uses the point of time when receiving the starting signal from the starting switch 8a as the starting point, and starts the prescribed rate feed pump 4 after 0.5 seconds from the starting point so as to feed the one paste at the fixed flow rate. Then, the control means 8 starts the prescribed rate feed pump 4 after 0.9 seconds from the starting point so as to feed the another paste at the flow rate corresponding to the mixing ratio of the both pastes of 1:3, that is, the flow rate being 3 times of that of the pump 4.

As a process for controlling the set rate feed pump 5 by the control means 8 so as to feed the paste at the flow rate corresponding to the mixing ratio selected and set by the mixing ratio selection switch 6, for example, the following process can be used when the prescribed rate feed pump 4 and the set rate feed pump 5 are a general pump, such as the rotary pump, the trochoid pump or the like, and the drive means for rotatively driving the pump is a general motor, such as a DC motor, an AD motor or the like. The out-putted rotational speed of the prescribed rate feed pump 4 can be controlled constantly by fixing the voltage when the drive means of the pump is the DC motor, or fixing the frequency of AC power supply when the drive means is the AC motor. Thereby, the flow rate of the one paste fed by the prescribed rate feed pump 4 can be controlled constantly. On the other hand, the out-putted rotational speed of the set rate feed pump 5 can be varied in two or more gradual rotational speed by changing the voltage of a variable transformer or the like when the drive means of the pump 5 is the DC motor, or changing the frequency of AC power supply of an inverter or the like when the drive means of the pump 5 is the AC motor. Thereby, the flow rate of the another paste fed by the set rate feed pump 5 can be controlled variable so as to have the flow rate gradually selected more than the flow rate of the pump 4. Then, the control means 8 can control for feeding the pastes at the flow rate corresponding to the mixing ratio selected and set by the mixing ratio selection switch 6.

As the control means 8, any one may be used if it can control as mentioned above. For example, the control means 8 comprises a switching circuit, a rotational frequency control circuit, a timer circuit, a signal processing circuit, or the like. The switching circuit is for controlling switching of power supply for supplying the power to the rotational axis for engaging the stirring rod 2a, the prescribed rate feed pump 4 and the set rate feed pump 5. The rotational frequency control circuit comprises the variable transformer, inverter or the like, which is for gradually changing the voltage or the frequency of AC power supply to the set rate feed pump 5. The timer circuit is for controlling the timing for starting the prescribed rate feed pump 4 and the set rate feed pump 5. The signal processing circuit is for receiving the signal from the starting switch 8a, the mixing ratio selection switch 6 or the like, collating the starting times of the prescribed rate feed pump 4 and the set rate feed pump 5 in the starting time memory means 7, and carrying out processing, such as an instruction with respect to these circuits or the like, according to the collated starting times.

9 is a dental impression material selection switch, which is for selecting and setting the arbitrary one dental impression material among the two or more sets of the dental impression material comprising the two kinds of pastes, where the pastes have the different fluidities at the time feed start. By the dental impression material selection switch 9, the device of the present invention can correspond to the dental impression material comprising the two kinds of pastes, in which the viscosity can be arbitrary adjusted by changing the mixing ratio of the both pastes in the two or more sets within the prescribed range.

In order to select and set the sets of the dental impression materials by the dental impression material selection switch 9, the starting time memory means 7 must be constituted such that the starting times of the prescribed feed pump 4 and the set rate feed pump 5 are prememorized about the two or more sets of the dental impression material comprising the two kinds of pastes, and the control means 8 must be constituted such that the starting times of the pump 4 and the pump 5, which are memorized in the starting time memory means 7, are collated about the selected and set dental impression material.

The starting time memory means 7 constituted in this way memorizes a data table corresponding to each item of the starting time about the two or more sets of the dental impression material, which is specified as shown in Tables 1-3. The arbitrary one dental impression material comprising the two kinds of pastes having the different fluidities at the time of the feed start is selected and set by the dental impression material selection switch 9 among the two or more sets of the dental impression material comprising the two kinds of pastes. The mixing ratio is selected and set by the mixing ratio selection switch 6. Then, the control means 8 collates the starting times of the prescribed rate feed pump 4 and the set rate feed pump 5 in the starting time memory means 7 from the data table of the selected and set dental impression material, and starts the pump 4 and the pump 5 according to the collated starting time of the dental impression material.

As the dental impression material selection switch 9, any one may be used, if it is for selecting and setting the arbitrary one dental impression material among the two or more sets of the dental impression material, and transmitting to the control means 8 what is the selected and set arbitrary one dental impression material, where the dental impression material comprises the two kinds of pastes having the different fluidities at the time of feed start. More particularly, as shown in FIG. 3, when the dental impression material selection switch 9 is, for example, a rotary changeover switch, the following switch can be suitably used. The switch comprises an electronic circuit where the two or more sets of the dental impression material are assigned to each contact point of the changeover switch and the contact point is electrified when the arbitrary one dental impression material is selected and set by rotating the changeover switch and, thereby, the control means 8 can recognize which dental impression material is selected and set among the two or more sets of the dental impression material. Further, the following switch can be also suitably used, as the mixing ratio selection switch 6. The switch comprises a dental impression material selection button, a display means, a dental impression material setting button and a dental impression material signal transmission means, where the dental impression material selection button is for changing the dental impression material one by one, the display means is for displaying the changed dental impression material one by one, the dental impression material setting button is for selecting and setting the dental impression material to the material displayed in the display means, and the dental impression material signal transmission means is for transmitting an information signal of the selected and set dental impression material to the control means 8.

Then, the using method of the dental impression material kneading device according to the present invention having the constitution above is explained.

First, as the preparation, an operation is carried out so as to have the state, in which each paste of the dental impression material comprising the two kinds of pastes having the different fluidities at the time of feed start, can be supplied from the containers Cx and Cy accommodating each paste to the inlets 1*x* and 1*y*. As shown in FIG. 3, this operation is carried out by, for example, engaging the discharge gates of the containers Cx and Cy with the inlets 1*x* and 1*y* respectively, where the containers Cx and Cy accommodate the two kinds of pastes of the dental impression material having the different fluidities at the time feed start.

Then, the set of the dental impression materials comprising the two kinds of pastes is selected and set by the dental impression material selection switch 9. At this time, the following mode must be specified. The starting times of the prescribed rate feed pump 4 and the set rate feed pump 5 about the two or more sets of the dental impression material comprising the two kinds of pastes having the different fluidities at the time of feed start are prememorized in the starting time memory means 7, where the starting times correspond to the two or more gradual mixing ratios of the both pastes. Further, the control means 8 can collate the starting times of the pump 4 and the pump 5 memorized in the starting time memory means 7 about the dental impression material selected and set by the dental impression material selection switch 9. The dental impression material selection switch is for selecting and setting the arbitrary one dental impression material comprising the two kinds of pastes having the different fluidities in the two or more sets of the dental impression material.

Further, the mixer body M is mounted to the mixer body mounting part 2. This operation is carried out by mounting the stirring rod K to the rotational axis for engaging the stirring rod 2*a* projected on the central axis of the mixer body mounting part 2 at first, and mounting the outer case S to the outer case mounting part 2*b* of the mixer body mounting part 2.

After finishing such the preparations, at first, the mixing ratio of the both pastes are selected and set to the arbitrary one mixing ratio among the two or more gradual mixing ratios by the mixing ratio selection switch 6.

Then, the dental impression material comprising the two kinds of pastes having the different fluidities is mixed and kneaded with the desired mixing ratio by transmitting of the signal for starting the mixing and kneading to the control means 8. The desired mixing ratio is selected and set by the mixing ratio selection switch 6 and the transmitting the signal is carried out through the starting switch 8*a*.

At this time, when receiving the signal for starting the mixing and kneading from the starting switch 8*a*, the control means 8 starts the drive means for rotatively driving the rotational axis for engaging the stirring rod 2*a*, collates the starting times of the prescribed rate feed pump 4 and the set rate feed pump 5 in the starting time memory means 7, starts the pump 4 and the pump 5 according to the collated starting times, and controls the pump 5 so as to feed the paste at the flow rate corresponding to the mixing ratio, where the collated starting times correspond to the mixing ratio based on the arbitrary one mixing ratio selected and set among the two or more gradual mixing ratio by the mixing ratio selection switch 6. Then, as the result, the both pastes are simultaneously discharged into the outer case S of the mixer body M with the desired mixing ratio selected and set by the mixing ratio selection switch 6, and thus it is possible to make the dental impression material comprising the two kinds of pastes having the desired mixing ratio and the preferable mixing and kneading state in the initial state of the mixing and kneading.

When the both pastes are simultaneously discharged into the outer case S of the mixer body M with the desired mixing ratio selected and set by the mixing ratio selection switch 6 in this way, the both pastes are mixed and kneaded by the stirring rod K in the mixer body M, where the stirring rod K is rotatively driven by the stirring axis for engaging the stirring rod 2*a*. Then, the prescribed rate feed pump 4 and the set rate feed pump 5 successively feed each paste accommodated in the containers Cx and Cy, and discharged each paste into the outer case S of the mixer body M from the outlets 3*x* and 3*y*. Then, the dental impression material mixed and kneaded in the outer case S of the mixer body M is pushed out and discharged from the discharging gate S1, which is provided at the end part of the outer case S of the mixer body M.

When receiving a signal for stopping the mixing and kneading by an operation of the starting switch 8*a* after discharging of the dental impression material in the desired amount from the discharging gate S1 in this way, the control means 8 stops the rotative drive of the rotational axis for engaging the stirring rod 2*a,* and stops the prescribed rate feed pump 4 and the set rate feed pump 5. Thus, it is possible to make the dental impression material comprising the two kinds of pastes having a desired mixing ratio, a preferable mixing and kneading state in the initial state of the mixing and kneading, and a desired amount.

Further, in the case that the dental impression material having the different mixing ratio of the both pastes is wanted further after having made the dental impression material having the a desired mixing ratio, a desired amount and a preferable mixing and kneading state, arbitrary another mixing ratio of the both pastes is selected and set by the mixing ratio selection switch 6 among the two or more gradual mixing ratios, and the signal for starting the mixing and kneading is transmitted again by the operation of the starting switch 8*a*. Then, the dental impression material having the different mixing ratio of the both pastes can be obtained easily.

Further, in the case that the operation of the mixing and kneading by the device of the present invention is not carried out for a while, the outer case S of the mixer body M is removed from the outer case mounting part 2*b* of the mixer body mounting part 2. Then, the stirring rod K in the mixer body M is removed from the rotational axis for engaging the stirring rod 2*a* of the mixer body mounting part 2. Then, the paste remained in the outer case S or the stirring rod K in the mixer body M is removed. Thus, the mixer body can be used readily whenever using the device of the present invention next time.

At this time, if the control means 8 controls so as to stop the rotative drive of the rotational axis for engaging the stirring rod 2*a* after passing a while, for example, for about several seconds, after stopping the prescribed rate feed pump 4 and the set rate feed pump 5, when receiving the signal for stopping the mixing and kneading by operation of the starting switch 8a, the both pastes remain in the outer case S or the stirring rod K in the mixer body M with the preferable mixing and kneading state. Thus, the cleaning workability of the inside of the outer case S or the stirring rod K after using can be remarkably enhanced, so that it is preferable.

What is claimed is:

1. A dental impression material kneading device for discharging each paste of a dental impression material including two kinds of pastes having different fluidities at the time of feed start, with a mixing ratio selected and set among two or more gradual mixing ratios, and for mixing and kneading the both pastes in a mixer body, the dental impression material kneading device comprising:
   a stirring rod configured to rotate about an axis of rotation;
   an outer case;
   first and second inlets where each paste is fed from first and second containers accommodating each paste, respectively;
   first and second outlets provided at a mixer body mounting part including the outer case mounting part through which the stirring rod configured to rotate about an axis of rotation projects, wherein said outer case mounting part is configured to detachably couple to said outer case;
   a prescribed rate feed pump configured to feed one paste from said first inlet to said first outlet at a fixed flow rate;
   a set rate feed pump configured to feed another paste from said second inlet to said second outlet at a flow rate gradually selected to be more than said flow rate of the prescribed rate feed pump;
   a mixing ratio selection switch configured to select and set an arbitrary mixing ratio of both pastes from among the two or more gradual mixing ratios;
   a starting time memory configured to store starting times of said prescribed rate feed pump and said set rate feed pump, where these times correspond to the two or more gradual mixing ratios of both pastes; and
   a control means configured to
      rotatively drive the stirring rod upon receiving a signal for starting the mixing and kneading of the both pastes from a starting switch configured to transmit the signal;
      collate the starting times stored in said starting time memory, where said starting times correspond to the mixing ratio selected and set by said mixing ratio selection switch,
      start said prescribed rate feed pump and said set rate feed pump according to the collated starting times, and
      control said set rate feed pump so as to feed the paste at a flow rate corresponding to the mixing ratio selected and set by said mixing ratio selection switch.

2. The dental impression material kneading device according to claim 1, wherein
   the starting times of the prescribed rate feed pump and the set rate feed pump corresponding to the two or more gradual mixing ratios of both pastes are pre-stored in the starting time memory with respect to two or more sets of the dental impression material comprising the two kinds of pastes having the different fluidities at the time of feed start, and
   the control means is configured to collate the starting times stored in the starting time memory, start said prescribed rate feed pump and said set rate feed pump according to the collated starting times, and control said set rate feed pump so as to feed the paste at a flow rate corresponding to the mixing ratio selected and set by the mixing ratio selection switch, with respect to a dental impression material selected and set by a dental impression material selection switch configured to select and set one of said two or more sets of the dental impression material.

3. The dental impression kneading device according to claim 1, further comprising blades connected to the stirring rod.

4. The dental impression kneading device according to claim 3, wherein the blades are disposed inside the mixer body.

5. The dental impression kneading device according to claim 4, wherein the blades are disposed between the first and second outlets and the outer case.

6. The dental impression kneading device according to claim 5, wherein the outer case has a first inside diameter smaller than a second inside diameter of the outer case.

7. The dental impression kneading device according to claim 1, wherein the stirring rod extends through the mounting part into the mixer body and terminates inside the mixer body.

* * * * *